US 6,199,605 B1

(12) United States Patent
Inaba et al.

(10) Patent No.: US 6,199,605 B1
(45) Date of Patent: Mar. 13, 2001

(54) MEDIUM DISPENSING APPARATUS AND A METHOD FOR THE SAME

(75) Inventors: Kazuhiro Inaba; Toshiyuki Wakasa; Mamoru Shiratori; Masato Ichikawa, all of Tokyo (JP)

(73) Assignees: Nittetsu Mining Co., Ltd.; Sankyo Company, Limited, both of Tokyo (JP)

( * ) Notice: Subject to any disclaimer, the term of this patent is extended or adjusted under 35 U.S.C. 154(b) by 0 days.

(21) Appl. No.: 09/446,664

(22) PCT Filed: Jun. 22, 1998

(86) PCT No.: PCT/JP98/02770

§ 371 Date: Dec. 23, 1999

§ 102(e) Date: Dec. 23, 1999

(87) PCT Pub. No.: WO98/59032

PCT Pub. Date: Dec. 30, 1998

(30) Foreign Application Priority Data

Jun. 23, 1997 (JP) .................................... 9-166124
Mar. 19, 1998 (JP) .................................. 10-070474

(51) Int. Cl.[7] .................................................. B65B 43/42
(52) U.S. Cl. ........................ 141/181; 141/130; 422/100; 435/286.4; 435/305.1
(58) Field of Search .................................. 141/1, 11, 69, 141/130, 171, 181, 250, 272, 275, 276, 277, 278, 280, 281, 283; 422/100, 63, 66; 435/305.1, 288.3, 309.1, 309.4, 286.4

(56) References Cited

U.S. PATENT DOCUMENTS 3,844,896 * 10/1974 Sharpe .............................. 435/286.4
4,287,301 * 9/1981 Astle .
5,567,595 * 10/1996 Kok ..................................... 422/100
5,591,627 * 1/1997 Miyamoto ......................... 435/305.1
5,698,260 * 12/1997 Roth et al. ............................ 427/235

FOREIGN PATENT DOCUMENTS 3-49676    3/1991  (JP) .
4-248980   9/1992  (JP) .
5-153961   6/1993  (JP) ............................. C12M/1/34
6-174732   6/1994  (JP) .

* cited by examiner

Primary Examiner—Gregory L. Huson
Assistant Examiner—Khoa Huynh
(74) Attorney, Agent, or Firm—Sughrue, Mion, Zinn, Macpeak & Seas, PLLC

(57) ABSTRACT

A dispensing apparatus is which, even when a small amount of a medium is to be dispensed, can satisfactorily dispense the medium. The medium dispensing apparatus (1) has: a laboratory dish transporting mechanism (20) which transports a laboratory dish (10) along a predetermined path; a movable table (30) which is disposed in the laboratory dish transportation path by the laboratory dish transporting mechanism (20), with being upward inclined by a given angle θ toward a downstream side in a transportation direction of the laboratory dish (10), and which moves in circular motion in a horizontal plane along predetermined forward and backward directions, thereby moving the laboratory dish (10) placed on the table in circular motion along a horizontal direction, and in the forward and backward directions, in a state where the laboratory dish is upward inclined toward the downstream side in the transportation direction; and a medium dispensing mechanism (50) for dispensing a given amount of a medium to a portion in the laboratory dish (10) placed on the movable table (30), in a manner that at least part of the dispensed medium makes contact with the inner face of the side wall of the laboratory dish (10), the portion being on the downstream side in the transportation direction with respect to the center of the laboratory dish.

6 Claims, 18 Drawing Sheets

MEDIUM DISPENSING APPARATUS AND A METHOD FOR THE SAME

TECHNICAL FIELD

The present invention relates to a medium dispensing apparatus for dispensing a medium such as an agar medium which may be used in various kinds of microbial tests, into a laboratory dish or mixing and diluting a specimen with such a medium, and also to a method for the same.

BACKGROUND ART

Generally, a medium such as an agar medium is widely used in: microbial tests in, for example, the medicinal industry and relating to GMP validation, such as a axenic test, a bacteria limiting test, an environmental falling bacteria test, a measurement of the titer (efficacy) of an antibiotic, a body fluid concentration measurement, and a preservation effect test; microbial tests in, for example, the food industry, and relating to a countermeasure of preventing contamination due to noxious bacteria based on HACCP, such as a viable cell count test, and a cell count test.

In the case where a body fluid concentration measurement of an antibiotic is to be performed in the medicinal industry, for example, 5 to 10 cc of a solid medium mixed with bacteria is dispensed into a laboratory dish, and a disk or a cup is then placed on the dispensing face. Thereafter, a specimen is infiltrated or dispensed into the disk or the cup, and the specimen is cultivated. The concentration of body fluid is then measured on the basis of the size of a region where the bacteria grow.

In the case where the titer of an antibiotic is to be measured, for example, 20 cc of a base layer medium (a medium to which nutrients are added so that bacteria eat by preference the medium to rapidly grow) is dispensed into a laboratory dish and solidified therein. Thereafter, 4 cc of a seed layer medium (a medium containing bacteria) is dispensed onto the base layer medium. A disk or a cup is then placed on the surface of the seed layer medium. An antibiotic of a known titer and that of an unknown titer are dispensed into the disk or the cup at different concentrations and cultivation is then performed. Thereafter, regions where bacteria grow are measured and the titer of the antibiotic in which the titer has not been known is calculated.

Such various kinds of microbial tests are roughly classified into a qualitative test and a quantitative test. In a quantitative test, an agar medium is always used.

In such various kinds of tests, when the sampling number of a specimen is large and plural types of media are used, a very long time period is required for sampling the specimen and dispensing the media. In order to enhance the test accuracy, the work of dispensing a medium must be performed in a sterilized room or the like.

An apparatus for automatically performing sampling of a specimen and the work of dispensing a medium is disclosed in, for example, Japanese Unexamined Patent Publications (Kokai) Nos. Hei. 5-153961, Hei. 4-248980, and Hei. 3-49676.

FIG. 20 is a view schematically showing the configuration of a medium dispensing, mixing and diluting apparatus 200. The dispensing, mixing and diluting apparatus 200 comprises a medium dispensing apparatus 201 which dispenses a medium material, and a mixing and agitating apparatus 202 which mixes and dilutes the medium material, and mixes a specimen diluent 203 with an agar medium 204 to automatically prepare a poured culture plate.

In the dispensing, mixing and diluting apparatus 200, first, empty laboratory dishes 206 which are accommodated in a vertical stacked state are extracted one by one from a rack 212, and sent onto a conveyor which is not shown, to be transported. With respect to each of the laboratory dishes 206 which are transported by the conveyor, a lid is opened and the specimen diluent 203 is then dispensed into the laboratory dish by a specimen diluent dispensing apparatus 209. The specimen diluent dispensing apparatus 209 sequentially dilutes the specimen in a test tube at plural steps of dilution ratio with a diluent, and dispenses the specimen diluent 203 into the laboratory dish 206 by means of a micro pipette 210.

Next, the medium dispensing apparatus 201 supplies a preset amount of the molten agar medium 204 from a medium dispensing nozzle 205 into the laboratory dish 206, via a medium tank (not shown), a circulation pipe (not shown), and a manifold (not shown).

In the mixing and agitating apparatus 202, an agitation plate 207 is rotated by a rotation mechanism 208, whereby the specimen diluent 203 which has been dispensed into the laboratory dish 206 by the specimen diluent dispensing apparatus 209, and the agar medium 204 which has been dispensed into the laboratory dish 206 by the medium dispensing apparatus 201 are mixed with each other and agitated. The specimen diluent 203 and the agar medium 204 which are mixed together are solidified by a cooling apparatus 211 to prepare a poured culture plate. Thereafter, the lid is put on the laboratory dish 206, and the laboratory dish is then accommodated in a rack 213 in a vertical stacked state.

Therefore, the above-described dispensing, mixing and diluting apparatus 200 can mix the specimen diluent 203 and the agar medium 204 at a given amount with each other and automatically prepare a poured culture plate. It is a matter of course that, when the step of dispensing the specimen diluent 203 is omitted and only the agar medium 204 is dispensed, it is possible to prepare a plate medium.

The dispensation and mixture and dilution of a medium are processed in different manners depending on the kind of a test in which the medium is used, and roughly classified into medium dispensations of four kinds, a plate medium, a poured culture plate, a multilayer medium, and a thin layer medium. A mixing and diluting step of mixing and agitating a specimen diluent and an agar medium is conducted only in preparation of a poured culture plate.

For a plate medium and a poured culture plate among the media, the above-described dispensing, mixing and diluting apparatus 200 can be used An dispensation and mixture and dilution. With respect to dispensation of a multilayer medium and a thin layer medium, however, the above-described dispensing, mixing and diluting apparatus 200 cannot perform automatic dispensation because the amount of the dispensed medium is small and the dispensed medium hardly spreads.

Specifically, in dispensation of the multilayer, the dispensation amount of the medium of the seed layer to be stacked is small (for example, about 4 cc), the medium hardly spreads in a uniform manner during dispensation, and the temperature of the base layer which is previously solidified is lowered to the vicinity of room temperature (usually, 20 to 24° C.). After dispensation, therefore, the medium must be promptly spread in a uniform manner.

In dispensation of the thin layer medium, because the dispensation amount of the medium is small (for example, about 5 cc), and the surface of a laboratory dish has water repellency owing to a silicone release agent which is used in molding of a plastic laboratory dish, there is a problem in that the medium hardly spreads in a uniform manner during dispensation.

Also with respect to dispensation and mixture and dilution of the plate medium and the poured culture plate, in the above-described dispensing, mixing and diluting apparatus 200, the fluidity is insufficient depending on the concentration of a medium on a laboratory dish, whereby a problem of reduced smoothness of the medium may be caused. When the temperature of a medium is kept high, the fluidity of the medium can be maintained so that even a small amount of the medium can be dispensed. When a medium is heated to 50° C. or higher, however, bacteria of the specimen die. During the work of dispensing or mixing and diluting a poured culture plate, a multilayer medium, and a thin layer medium, therefore, the temperature of a medium cannot be kept high so as to maintain the fluidity of the medium.

To comply with this, in the dispensing, mixing and diluting apparatus 200 of the conventional art, dispensation and mixture and dilution of a plate medium and a poured culture plate, and dispensation of a multilayer medium and a thin layer medium in which a small amount (for example, less than 7 cc) of the medium is used cannot be automated. Consequently, the dispensing work must be manually performed, thereby producing a problem in that it requires a great deal of labor and time.

Therefore, it is an object of the invention to provide a medium dispensing apparatus which can solve the above-discussed problems, in which, even when a small amount of a medium is to be dispensed, the medium can be satisfactorily dispensed, and an uneven thickness of the medium and the like can be surely prevented from occurring, and which can be satisfactorily used in dispensation of any of a plate medium, a poured culture plate, a multilayer medium, and a thin layer medium, and also a method for the same.

DISCLOSURE OF INVENTION

The object of the invention can be attained by a medium dispensing apparatus comprising:

transporting means for transporting a laboratory dish along a predetermined path;

a movable table which is disposed in the laboratory dish transportation path by the transporting means, with being upward inclined by a given angle toward a downstream side in a laboratory dish transportation direction, and which moves in circular motion in a horizontal plane along predetermined forward and backward directions, thereby moving a laboratory dish placed on the table in circular motion along a horizontal direction, and in the forward and backward directions, in a state where the laboratory dish is upward inclined toward the downstream side in the transportation direction; and medium dispensing means for dispensing a given amount of a medium to a portion in the laboratory dish placed on the movable table, in a manner that at least part of the dispensed medium makes contact with an inner face of a side wall of the laboratory dish, the portion being on the downstream side in the transportation direction with respect to a center of the laboratory dish.

Furthermore, the object of the invention can be attained by a method of dispensing a medium, characterized in that a laboratory dish is transported along a predetermined path by transporting means, and the laboratory dish is placed on a movable table which is disposed with being upward inclined by a given angle toward a downstream side in a laboratory dish transportation direction, under this state, a given amount of a medium is dispensed by medium dispensing means to a portion in the laboratory dish placed on the movable table, in a manner that at least part of the dispensed medium makes contact with an inner face of a side wall of the laboratory dish, the portion being on the downstream side in the transportation direction with respect to a center of the laboratory dish, and the movable table is moved in circular motion in a horizontal plane along predetermined forward and backward directions, thereby moving the laboratory dish placed on the table in circular motion along a horizontal direction, and in the forward and backward directions, in a state where the laboratory dish is upward inclined toward the downstream side in the transportation direction.

According to this configuration, a given amount of a medium is dispensed by the medium dispensing means to a portion in the laboratory dish placed on the movable table and on the downstream side in the transportation direction with respect to the center of the laboratory dish, in a manner that at least part of the dispensed medium makes contact with the inner face of the side wall of the laboratory dish. The laboratory dish placed on the table is moved in circular motion along a horizontal direction, and in the forward and backward directions, in a state where the laboratory dish is upward inclined toward the downstream side in the transportation direction. As a result, flows of different directions are produced in the medium, and a flow of one direction collides with flows of other directions, so that the medium is uniformly dispensed.

Furthermore, the object of the invention can be attained by a method of dispensing a medium in which a laboratory dish is transported along a predetermined path by transporting means, and the laboratory dish is placed on a movable table which is disposed in the transportation path, under this state, a given amount of a medium is ejected from a medium dispensing nozzle of medium dispensing means into the laboratory dish placed on the movable table, and the movable table is moved in circular motion in a horizontal plane along predetermined forward and backward directions, thereby dispensing the medium into the laboratory dish placed on the movable table, the method being characterized in that a relative position of the medium dispensing nozzle with respect to the movable table, a shape of the medium dispensing nozzle, and a pressure of ejecting the medium from the medium dispensing nozzle are suitably set, whereby the medium dispensed by the medium dispensing nozzle into the laboratory dish is dispensed to reach a whole inner face of a side wall of the laboratory dish at a substantially same time.

According to this configuration, the force of dispensing a medium by the medium dispensing nozzle causes the medium to move in radial directions of the laboratory dish, so that the medium reaches the whole inner face of the side wall of the laboratory dish at a substantially same time, and the movable table is moved in circular motion, whereby the medium is spread uniformly.

Furthermore, the object of t he invention can be attained by a medium dispensing apparatus comprising:

transporting means for transporting a laboratory dish along a predetermined path;

a movable table which is disposed in the laboratory dish transportation path by the transporting means, which moves in circular motion in a horizontal plane along predetermined forward and backward directions, in a state where the table is inclined by a given angle with respect to a horizontal plane, and which changes an inclination direction along a peripheral direction of the circular motion in a horizontal plane in predetermined forward and backward directions, thereby causing the placed laboratory dish to perform rocking motion in which the circular motion and the change of the inclination direction are combined with each other; and medium dispensing means for dispensing a given amount of a medium into the laboratory dish placed on the movable table.

Furthermore, the object of the invention can be attained by a method of dispensing a medium, characterized in that a laboratory dish is transported along a predetermined path by transporting means, and the laboratory dish is placed on a movable table which is disposed in a laboratory dish transportation path by the transporting means, under this state, a given amount of a medium is dispensed by medium dispensing means into the laboratory dish placed on the movable table, and the movable table is moved in circular motion in a horizontal plane along predetermined forward and backward directions, in a state where the table is inclined by a given angle with respect to a horizontal plane, and a direction of the inclination is changed along a peripheral direction of the circular motion in a horizontal plane in predetermined forward and backward directions, whereby the laboratory dish placed on the movable table is caused to perform rocking motion in which the circular motion and the change of the inclination direction are combined with each other.

In a preferred embodiment, the dispensing means dispenses a given amount of the medium to a portion in the laboratory dish placed on the movable table, in a manner that at least part of the medium makes contact with an inner face of a side wall of the laboratory dish, the portion being higher in level than a center of the laboratory dish.

In another preferred embodiment, the dispensing means dispenses a given amount of the medium into the laboratory dish placed on the movable table in a reference position. The term "reference position" in the present invention means a fixed peripheral stop position which is previously determined with respect to the movable table that moves in circular motion in a horizontal plane.

According to this configuration, the movable table in which the inclination angle is maintained causes the laboratory dish which is placed on the movable table and to which a given amount of a medium is dispensed by the medium dispensing means, to perform rocking motion in which the circular motion along a horizontal direction in the forward and backward directions, and a motion of changing the inclination direction along the peripheral direction of the circular motion in a horizontal plane in the forward and backward directions are combined with each other. As a result, flows of different directions are produced in the medium, and a flow of one direction collides with flows of other directions, so that the medium is uniformly dispensed.

According to the medium dispensing apparatus and the method for the same of the present invention, even when a small amount of a medium is used, therefore, dispensation of the medium or mixture and dilution with a specimen can be uniformly performed, and an uneven thickness of the medium and the like can be surely prevented from occurring.

In other words, the work of dispensing any of a plate medium, a poured culture plate, a multilayer medium, and a thin layer medium can be automated. Therefore, the workability of such a dispensing work, the accuracy of a test, and the reliability can be improved.

BEST MODE FOR CARRYING OUT THE INVENTION

Hereinafter, an embodiment of the invention will be described in detail with reference to the accompanying drawings.

Figure 1:
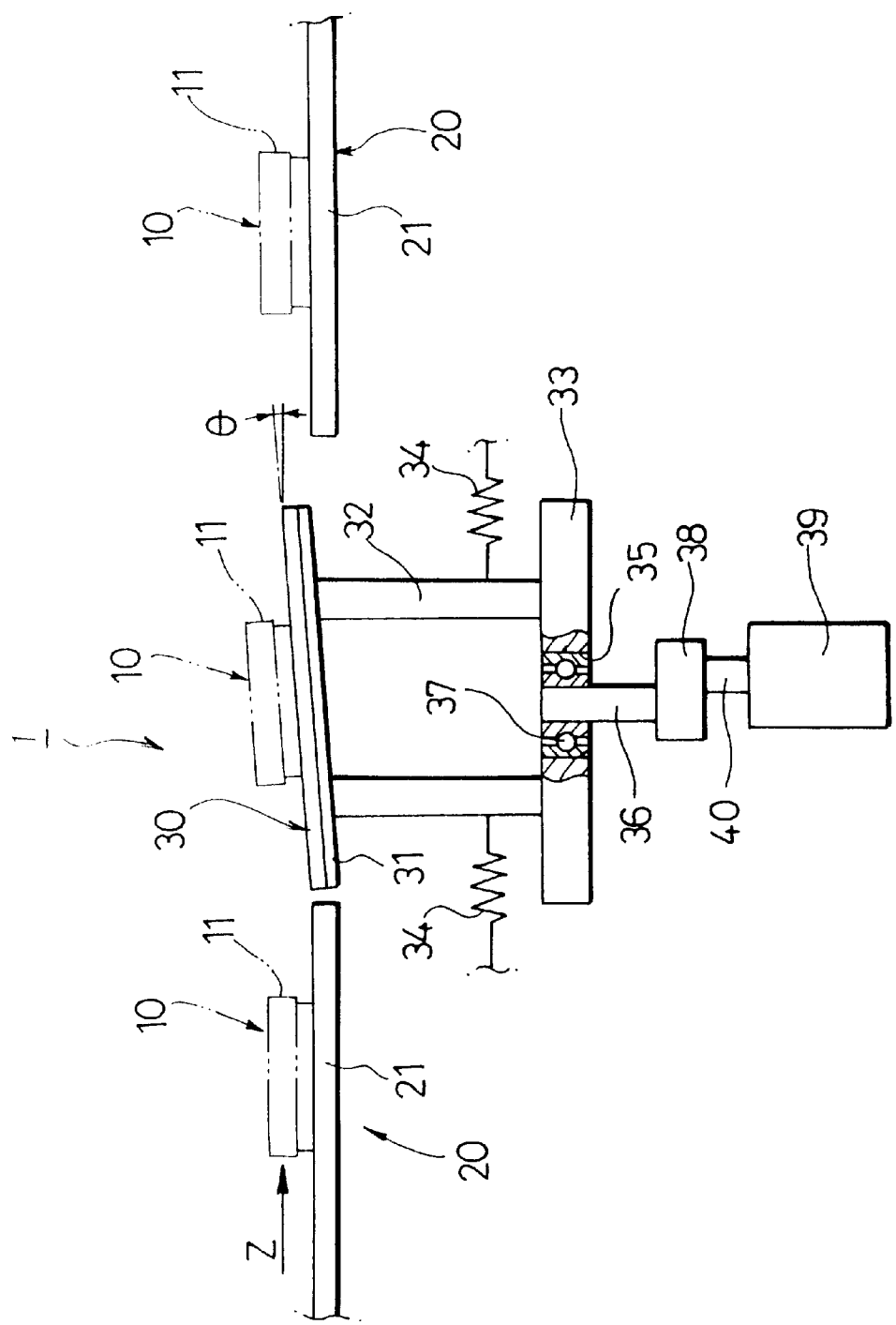
FIG. 1 is a schematic side view showing a movable table of a medium dispensing apparatus which is a first embodiment of the present invention.
Figure 2:
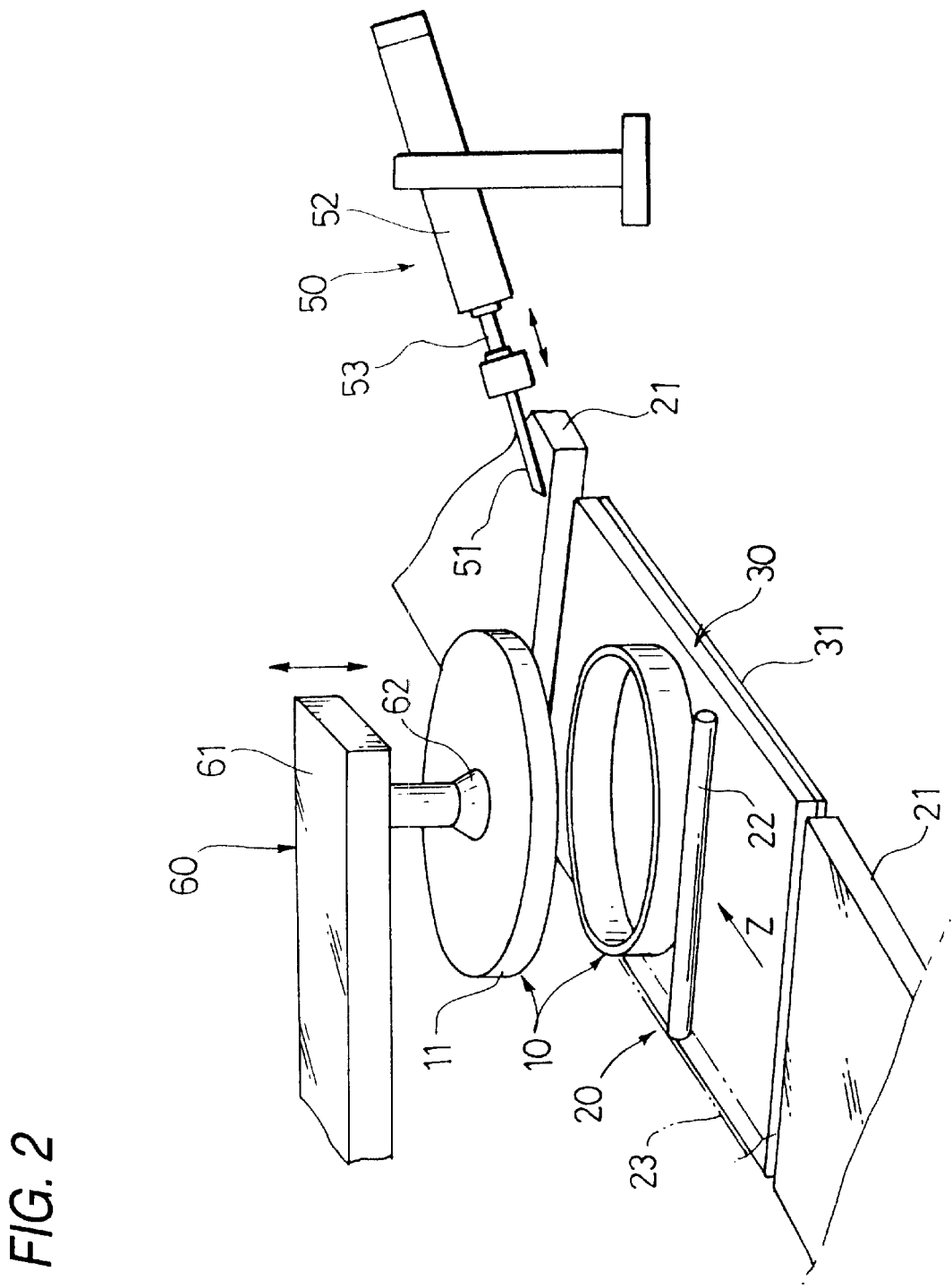
FIG. 2 is a perspective view showing medium dispensing means and a lid holding mechanism of the medium dispensing apparatus shown in FIG. 1.

As shown in FIGS. 1 and 2, in a medium dispensing apparatus 1 which is a first embodiment of the invention, a medium such as an agar medium is dispensed by medium dispensing means 50 into a laboratory dish 10 having a diameter of about 10 cm which is transported to a movable table 30 by a laboratory dish transporting mechanism 20 serving as transporting means. The medium in the laboratory dish 10 is uniformly spread by predetermined planar circular motion of the movable table 30.

The laboratory dish transporting mechanism 20 transports the laboratory dish 10 placed on a transportation path 21, along a predetermined direction (transportation direction Z) with pushing the laboratory dish by a transportation bar member 22. The transportation bar member 22 is fixed at predetermined intervals to an endless chain 23 which is wound around a sprocket (not shown), and moved along a predetermined path by movement of the endless chain 23 due to rotation of the sprocket which is driven by driving means (not shown).

In the transportation path of the laboratory dish 10 by the laboratory dish transporting mechanism 20, the movable table 30 comprises a support plate 31 which is upward inclined by a given angle θ (for example, θ=4°) toward the downstream side in the transportation direction Z of the laboratory dish 10, and which constitutes a part of the transportation path 21. Furthermore, the movable table 30 moves in circular motion in a horizontal plane along predetermined forward and backward directions, thereby enabling the laboratory dish 10 placed on the support plate 31 to be moved in circular motion in a state where the laboratory dish is upward inclined by the angle θ toward the downstream side in the transportation direction, along a horizontal direction, and for a predetermined time period in each of the forward and backward directions (for example, 2 seconds in each of the forward and backward directions).

As shown in FIG. 1, the support plate 31 of the movable table 30 is fixed to a base plate 33 via columns 32. Spring members 34 which are placed in a substantially horizontal direction are coupled to approximately middle portions of the columns 32, respectively. The horizontal movements of the columns 32 are elastically restricted within a predetermined range by the spring members 34, respectively.

Through a penetrated hole 35 opened in a substantially center portion of the base plate 33 to which the columns 32 are fixed, a tip portion of a shaft 36 is fittingly inserted so as to be relatively rotatable via a bearing 37. The shaft protrudes from the upper face of an eccentric rotating plate 38 which is fixed in a state where the plate is off-centered by a given amount with respect to a rotation shaft 40 of a motor 39.

The base plate 33 is supported so as to be movable in a horizontal plane. When the eccentric rotating plate 38 is eccentrically rotated in accordance with rotation of the motor 39, the base plate 33 can move in circular motion in the horizontal plane along predetermined forward and backward directions. In accordance with the circular motion of the base plate 33, therefore, the support plate 31 is moved in circular motion along a horizontal direction in the forward and backward directions, in a state where the plate is upward inclined toward a downstream side in the transportation direction.

As shown in FIG. 2, the medium dispensing means 50 ejects a given amount of the medium from a medium dispensing nozzle 51 in a predetermined direction and at a given pressure. Specifically, the medium dispensing nozzle 51 is attached to a tip end of a cylinder rod 53 of an air cylinder 52. When the medium is to be dispensed, the nozzle is projected in a predetermined direction toward the laboratory dish 10 in accordance with the operation of the air cylinder 52, and a given amount of the medium is ejected by a predetermined ejection pressure due to a medium dispensing pump (not shown) of the roller type or the syringe type.

The medium dispensing means 50 dispenses the medium into the laboratory dish 10 so that a pool of the medium is formed in the downstream side in the transportation direction Z with respect to the center of the laboratory dish 10 on the movable table 30 and at least part of the medium pool makes contact with the inner face of the side wall of the laboratory dish 10.

Figure 3A:
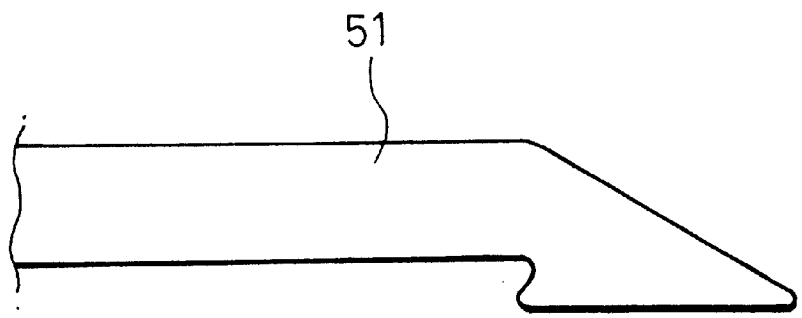
FIG. 3(a) and FIG. 3(b) are a side view and a bottom view showing the shape of a tip end of a medium dispensing nozzle of the medium dispensing means shown in FIG. 2.
Figure 3B:
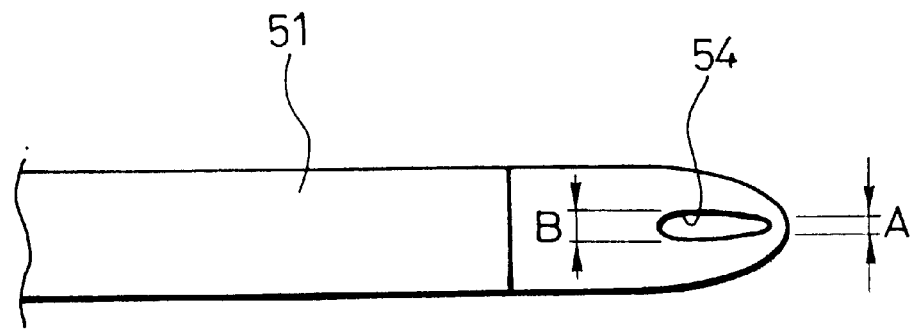

As shown in FIG. 3(a), the tip end of the medium dispensing nozzle 51 has a shape which is gradually widened in a side view as moving in the downward direction. As shown in FIG. 3(b), a passage opening 54 of the medium dispensing nozzle 51 is formed into an oval shape in which the longitudinal direction elongates along the flowing direction of the medium. For example, the dimension A is set to A=2 mm and the dimension B to B=2.5 mm.

As shown in FIG. 2, a lid holding mechanism 60 is disposed above the movable table 30. Before the medium is dispensed into the laboratory dish 10 by the medium dispensing means 50, the lid holding mechanism 60 sucks a lid 11 of the laboratory dish 10 on the movable table 30, by means of a suction disk 62 which is disposed at the tip end of a holding arm 61. In accordance with rising movement of the holding arm 61, the lid 11 is lifted and the lid 11 is then opened. After the medium is dispensed into the laboratory dish 10 and before circular motion is performed by the movable table 30, the lid holding mechanism 60 lowers the holding arm 61 and cancels the suction of the lid 11 by the suction disk 62, thereby causing the lid 11 to be put on the laboratory dish 10.

Next, the function of the medium dispensing apparatus 1 of the first embodiment will be described with reference to FIGS. 1 and 4 to 6.

When dispensation of a thin layer plate is to be performed by the medium dispensing apparatus 1 of the first embodiment, for example, the laboratory dish 10 supplied from a laboratory dish supplying section (not shown) is transported to the movable table 30 by the laboratory dish transporting mechanism 20, and then placed on the support plate 31.

Figure 4A:
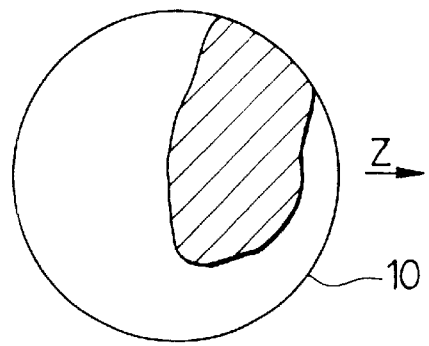
FIG. 4(a) to FIG. 4(d) are a plan view showing an example of a state change of a medium which is dispensed into a laboratory dish by the medium dispensing means of the medium dispensing apparatus of FIG. 1.
Figure 4B:
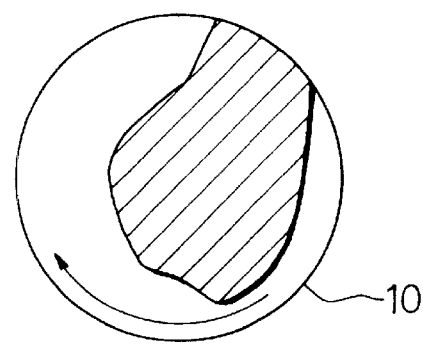
Figure 4C:
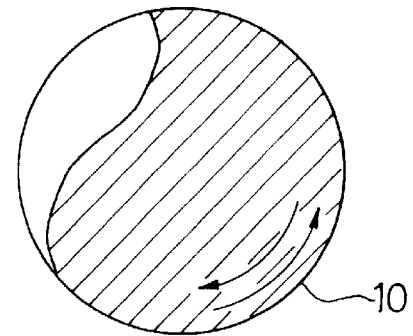
Figure 4D:
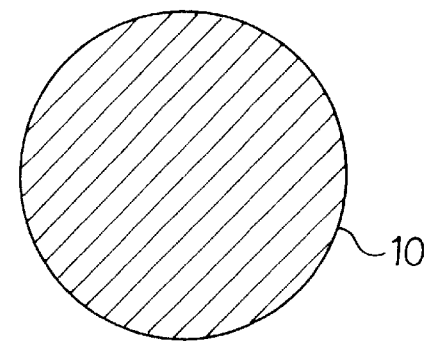
Figure 5A:
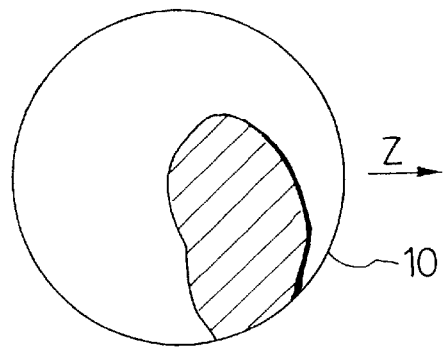
FIG. 5(a) to FIG. 5(d) are a plan view showing another example of a state change of a medium which is dispensed into a laboratory dish by the medium dispensing means of the medium dispensing apparatus of FIG. 1.
Figure 5B:
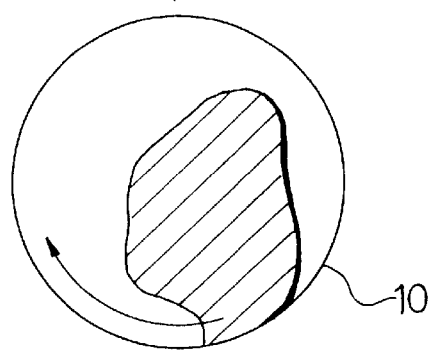
Figure 5C:
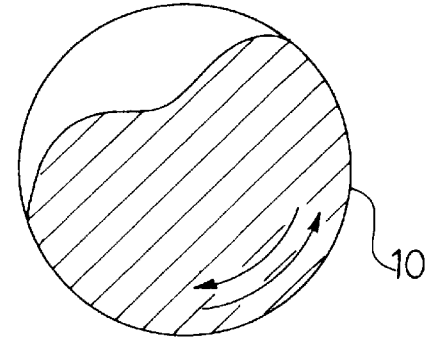
Figure 5D:
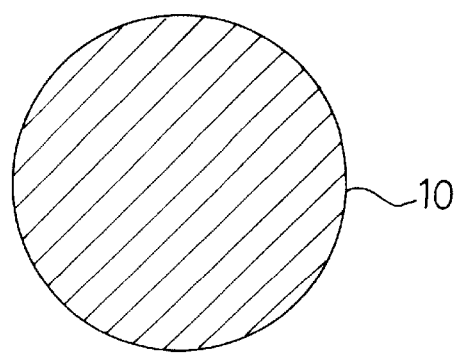
Figure 6A:
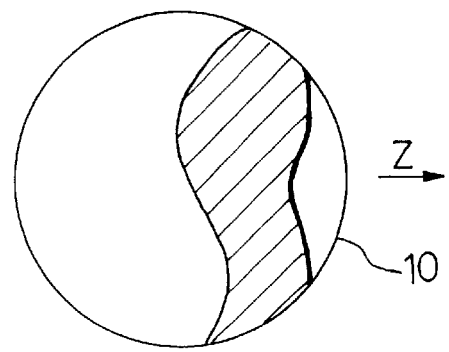
FIG. 6(a) to FIG. 6(d) are a plan view showing a further example of a state change of a medium which is dispensed into a laboratory dish by the medium dispensing means of the medium dispensing apparatus of FIG. 1.
Figure 6B:
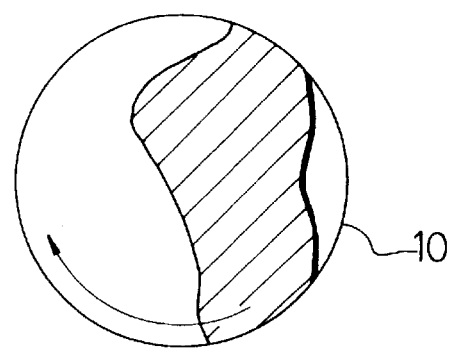
Figure 6C:
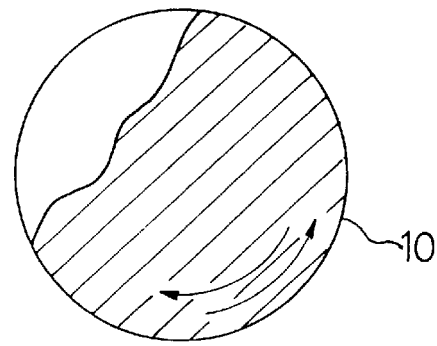
Figure 6D:
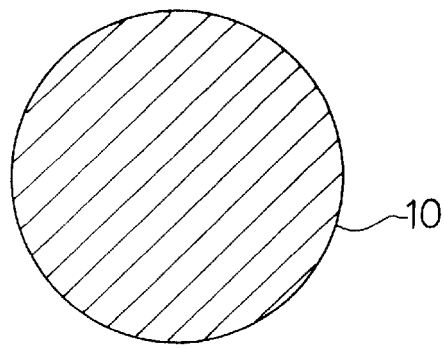

After the lid 11 is taken off by the lid holding mechanism 60, a given amount (about 5 cc) of the medium which previously contains viable cell is dispensed into the laboratory dish 10 on the movable table 30, from the medium dispensing nozzle 51 of the medium dispensing means 50. In this case, as shown in FIG. 4(a), 5(a), or 6(a), the medium dispensing means 50 dispenses the medium into the laboratory dish 10 so that a pool of the medium is formed in the downstream side in the transportation direction Z with respect to the center of the laboratory dish 10 and at least a part of the medium pool makes contact with the inner face of the side wall of the laboratory dish 10. In FIG. 4(*a*), a portion of the medium pool which is an upper portion in the figure makes contact with the inner face of the side wall of the laboratory dish 10. In FIG. 5(*a*), a portion of the medium pool which is a lower portion in the figure makes contact with the inner face of the side wall of the laboratory dish 10. In FIG. 6(*a*), portions of the medium pool which are upper and lower portions in the figure make contact with the inner face of the side wall of the laboratory dish 10.

Since the support plate 31 is upward inclined by the given angle θ toward the downstream side in the transportation direction Z, the dispensed medium flows in the laboratory dish 10 toward the upstream side in the transportation direction Z as shown in FIG. 4(*b*), 5(*b*), or 6(*b*).

The lid 11 is again put on the laboratory dish 10 to which the medium is dispensed, by the lid holding mechanism 60. Under this state, the movable table 30 is forward rotated for a predetermined time period (for example, 2 seconds), so that the laboratory dish 10 placed thereon is moved in circular motion in the forward direction along a horizontal direction under a state where the laboratory dish is upward inclined by the given angle θ toward the downstream side in the transportation direction. As a result, as shown in FIG. 4(*c*), 5(*c*), or 6(*c*), the medium flows so as to cover the downstream side in the transportation direction Z with respect to the center of the laboratory dish 10.

Next, the movable table 30 is backward rotated for a predetermined time period (for example, 2 seconds), so that the laboratory dish 10 placed thereon is moved in circular motion in the backward direction along a horizontal direction under a state where the laboratory dish is upward inclined by the given angle θ toward the downstream side in the transportation direction. As a result, as shown in FIG. 4(*d*), 5(*d*), or 6(*d*), the medium flows so as to cover the upstream side in the transportation direction Z with respect to the center of the laboratory dish 10, and uniformly spreads.

After the medium in the laboratory dish 10 is uniformly spread by the above-mentioned circular motion of the movable table 30, the laboratory dish 10 is immediately transported to the next horizontal stage in which horizontality is ensured, and then allowed to stand still in a horizontal state for a predetermined time period (for example, 8 seconds). As a result, the medium in the laboratory dish 10 is uniformly solidified without causing an uneven thickness or the like.

Thereafter, the laboratory dish 10 is transported to a label attaching section (not shown). In the label attaching section, a label (not shown) bearing required information in the form of a bar code, such as the kind of the bacteria, the specimen number, and the date of dispensation is attached to the laboratory dish. The laboratory dish 10 to which the label is attached is transported to a laboratory dish stacking and accommodating section (not shown) to be accommodated therein.

In the first embodiment, the case of dispensation of a thin layer plate has been described. It is a matter of course that the embodiment may be used in preference also in dispensation of any of a plate medium, a poured culture plate, a multilayer medium, and a thin layer medium.

Namely, according to the method of dispensing and mixing and diluting a medium of the present invention, a given amount of the medium is dispensed by the medium dispensing means 50 to a portion in the laboratory dish 10 placed on the movable table 30 and on the downstream side in the transportation direction with respect to the center of the laboratory dish, in a manner that at least part of the dispensed medium makes contact with the inner face of the side wall of the laboratory dish 10. The laboratory dish 10 placed on the movable table 30 is moved in circular motion in an upward inclined state toward the downstream side in the transportation direction, along a horizontal direction, and in the forward and backward directions. As a result, flows of different directions are produced in the medium, and a flow of one direction collides with flows of other directions, so that the medium is uniformly dispensed. Also a poured culture plate requiring a mixing and diluting step can be easily produced, and it is possible to surely prevent an uneven thickness of the medium and the like from occurring.

In the first embodiment, the support plate 31 is upward inclined by 4 deg. toward the downstream side in the transportation direction Z. The invention is not restricted to this. The inclination angle may be suitably selected in accordance with the kind of the agar medium, the dispensation amount, etc. The invention is not restricted to the configuration of the laboratory dish transporting mechanism 20, the movable table 30, and the medium dispensing means 50 of the first embodiment, and may be variously configured.

Figure 7A:
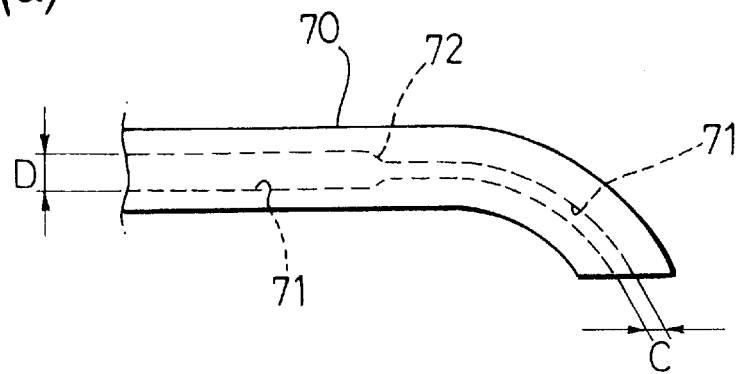
FIG. 7(a) to FIG. 7(b) are a side view and a bottom view showing the shape of a tip end of a medium dispensing nozzle of medium dispensing means of a medium dispensing apparatus which is a second embodiment of the invention.
Figure 7B:
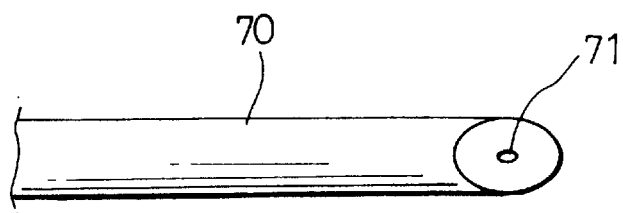
Figure 8:
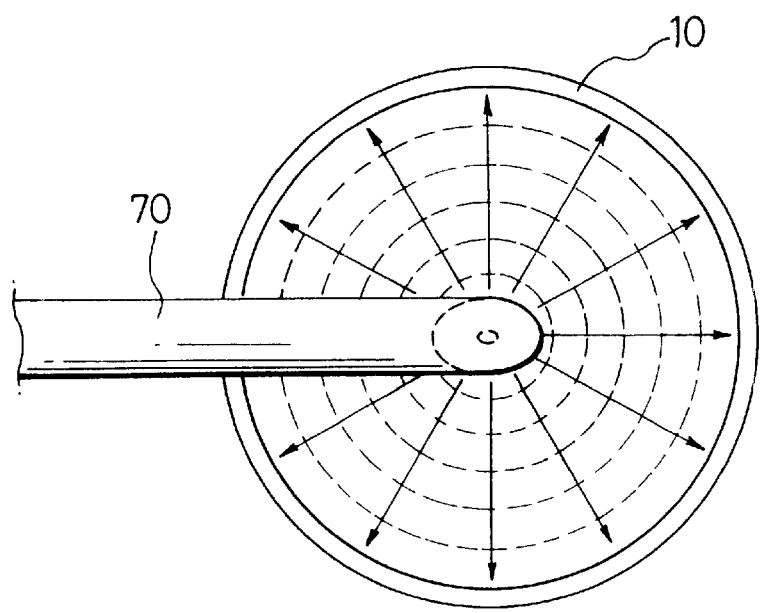
FIG. 8 is a plan view showing the medium dispensing nozzle shown in FIG. 7 and a state change of a medium which is dispensed into a laboratory dish.
Figure 9:
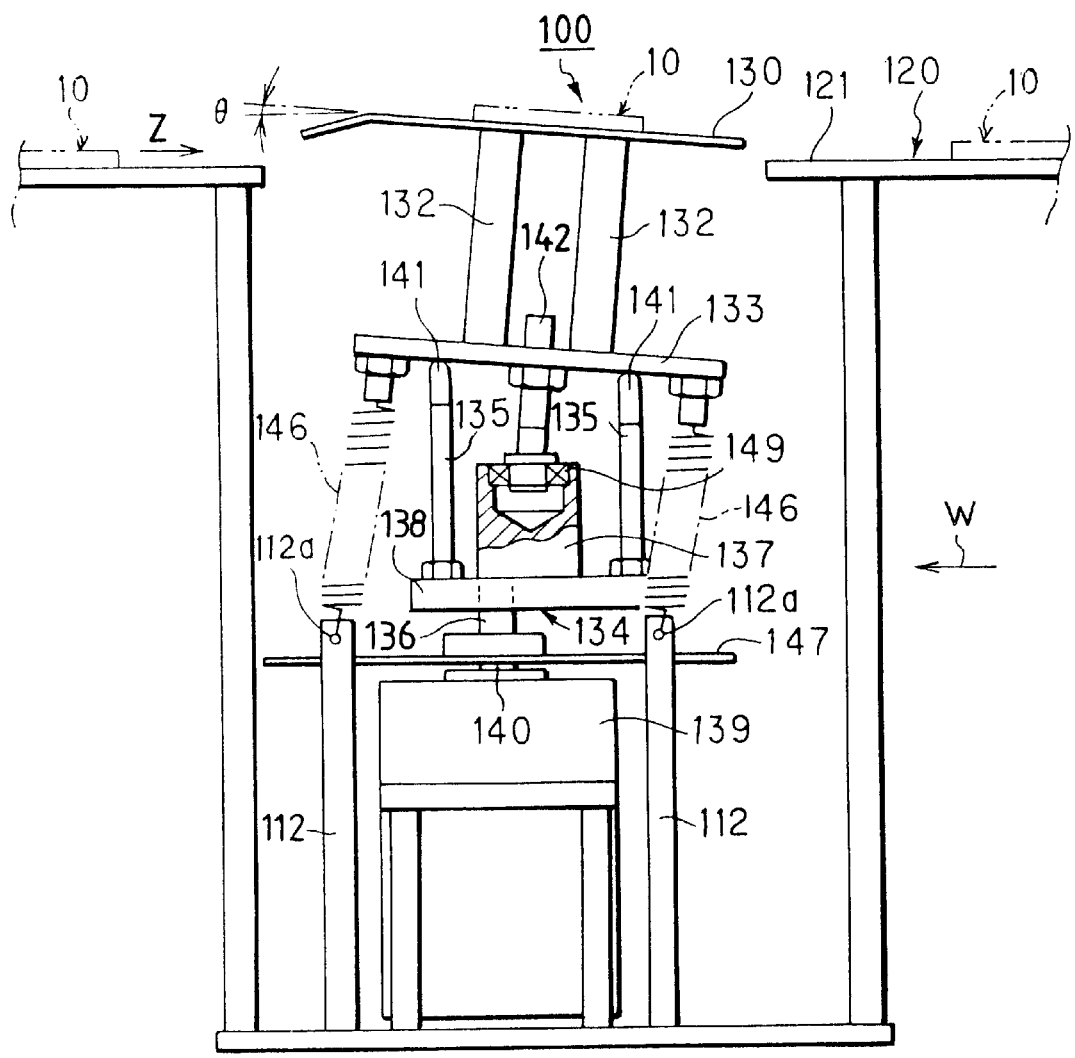
FIG. 9 is a schematic side view showing a movable table of a medium dispensing apparatus which is a third embodiment of the invention.

As shown in FIGS. 7 and 8, in a medium dispensing apparatus which is a second embodiment of the invention, the relative position of a medium dispensing nozzle 70 with respect to a movable table (not shown) which is horizontally disposed, the shape of the medium dispensing nozzle 70, and the pressure of ejecting a medium from the medium dispensing nozzle 70 are suitably set, and the medium dispensed by the medium dispensing nozzle 70 into the laboratory dish 10 is dispensed to reach the whole inner face of the side wall of the laboratory dish 10 at a substantially same time. In FIG. 8, the arrows indicate the spreading directions of the medium.

In the case of a multilayer dispensation, for example, the medium of the base layer is dispensed and solidified, and a given amount (for example, 4 cc) of the medium of the seed layer is then dispensed and dispersed. At dispensation of the seed layer, the seed layer tends to be solidified immediately after dispensation because the temperature of the base layer which is previously solidified is lowered to room temperature (22 to 25° C.) and the solidification temperature of an agar medium is usually in the vicinity of 37° C. Therefore, a medium passage 71 of the medium dispensing nozzle 70 is formed into a required shape in which the diameter of the passage is reduced in a region starting from a predetermined place 72 (for example, the passage diameter C on the side of the tip end=4 mm, the passage diameter D on the side of the basal end=6 mm), so that the force exerted in dispensation causes the medium of the seed layer to move in radial directions of the laboratory dish 10. Consequently, the medium of the seed layer which moves over that of the base layer that is hydrophilic reaches the whole inner face of the side wall of the laboratory dish 10 at a substantially same time.

When dispensation is ended, the lid is immediately put on, and the movable table is moved in circular motion along a horizontal direction in the forward and backward directions for a predetermined time period (for example, 2 seconds in the forward direction, and 2 seconds in the backward direction), thereby promoting the spread of the medium of the seed layer over that of the base layer. As a result, the medium of the seed layer can uniformly spread.

In the embodiment, during multilayer dispensation, the force of dispensing the medium by the medium dispensing nozzle 70 having the above-described shape causes the medium to move over the hydrophilic medium of the base layer in radial directions of the laboratory dish 10, so that the medium reaches the whole inner face of the side wall of the laboratory dish 10 at a substantially same time, and the movable table is moved in circular motion, whereby the medium of the seed layer is spread uniformly. Even when a small amount (for example, about 4 cc) of the medium of the seed layer to be stacked is used, therefore, the medium of the seed layer can be uniformly spread, and an uneven thickness of the medium and the like can be surely prevented from occurring.

The invention is not restricted to the shape of the medium dispensing nozzle 70 in the second embodiment. It is a matter of course that any shape may be employed as far as it allows the medium dispensed by the medium dispensing nozzle into the laboratory dish, to be dispensed so as to reach the whole inner face of the side wall of the laboratory dish at a substantially same time.

As shown in FIGS. 9 to 15, in a medium dispensing apparatus 100 which is a third embodiment of the invention, a medium such as an agar medium is dispensed by medium dispensing means 150 into a laboratory dish 10 having a diameter of about 10 cm which is transported to a movable table 130 by a laboratory dish transporting mechanism 120 serving as transporting means. The medium in the laboratory dish 10 is uniformly spread by rocking motion of the movable table 130 in which predetermined planar circular motion and the change of the inclination direction are combined with each other.

The laboratory dish transporting mechanism 120 transports the laboratory dish 10 placed on a transportation path 121, along a predetermined direction (transportation direction Z) with pushing the laboratory dish by a transportation bar member 122. The transportation bar member 122 is fixed at predetermined intervals to an endless chain 123 which is wound around a sprocket (not shown), and moved along a predetermined path by movement of the endless chain 123 due to rotation of the sprocket which is driven by driving means (not shown).

Figure 10:
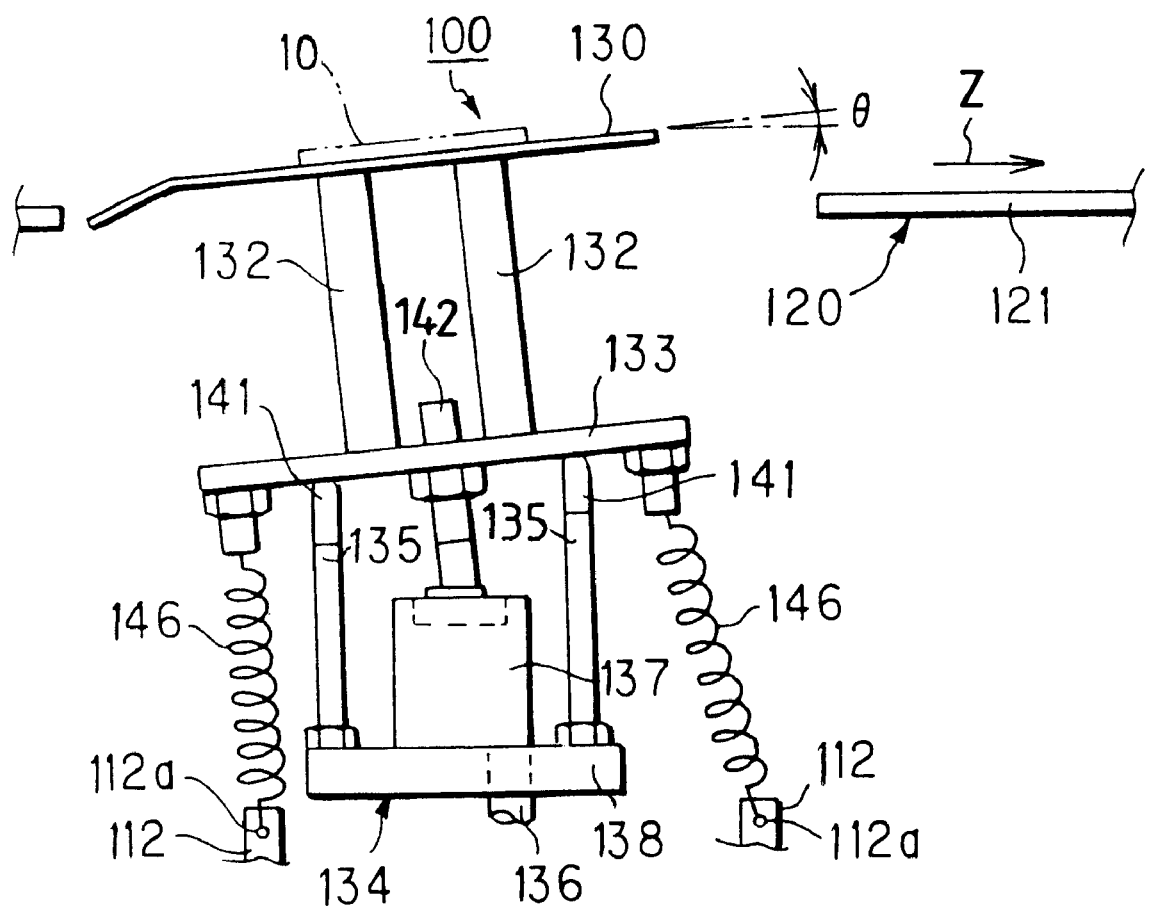
FIG. 10 is a schematic side view showing a state where an inclination angle of the movable table shown in FIG. 9 is changed by 180 degree in a horizontal plane.

In the transportation path of the laboratory dish 10 by the laboratory dish transporting mechanism 120, the movable table 130 constitutes a part of the transportation path 121 under a state shown in FIG. 10 (hereinafter, referred to as the reference position) where the table is upward inclined by a given angle θ (for example, θ=4°) from a horizontal plane toward the downstream side in the transportation direction Z of the laboratory dish 10.

Furthermore, the movable table 130 moves in circular motion in a horizontal plane along predetermined forward and backward directions, and changes the inclination direction along the peripheral direction of the circular motion in a horizontal plane from the reference position in predetermined forward and backward directions, while maintaining the inclination angle θ. As a result, the movable table 130 enables the placed laboratory dish 10 to perform rocking motion in which the circular motion and the change of the inclination direction are combined with each other, for a predetermined time period in each of the forward and backward directions (for example, 2.5 seconds in the forward direction, stop of 0.5 seconds, and 2.5 seconds in the backward direction). The stop position of the movable table 130 is controlled by a motor which will be described later, on the basis of a signal from a constant-position detecting sensor 131 (see FIG. 11), so as to be always placed in the reference position.

As shown in FIGS. 9 to 12, the movable table 130 is fixed to a base plate 133 via columns 132 in a substantially parallel state. By means of circular motion along forward and backward directions and a change of the inclination direction due to rotation of an eccentric rotating crank 134 and support rods 135, the movable table 130 causes the laboratory dish 10 placed thereon to perform rocking motion in which the circular motion and the change of the inclination direction are combined with each other.

The eccentric rotating crank 134 consists of: a shaft 136 which is coupled to a rotation shaft 140 of the motor 139; an eccentric rotating plate 138 which is fixed to the shaft 136 in a state where the plate is off-centered by a given amount; and a boss portion 137 which is projected from a substantially center portion of the upper face of the eccentric rotating plate 138. The eccentric rotating plate 138 and the boss portion 137 are eccentrically rotated by rotation of the shaft 136 due to rotation of the rotation shaft 140 of the motor 139.

Figure 12:
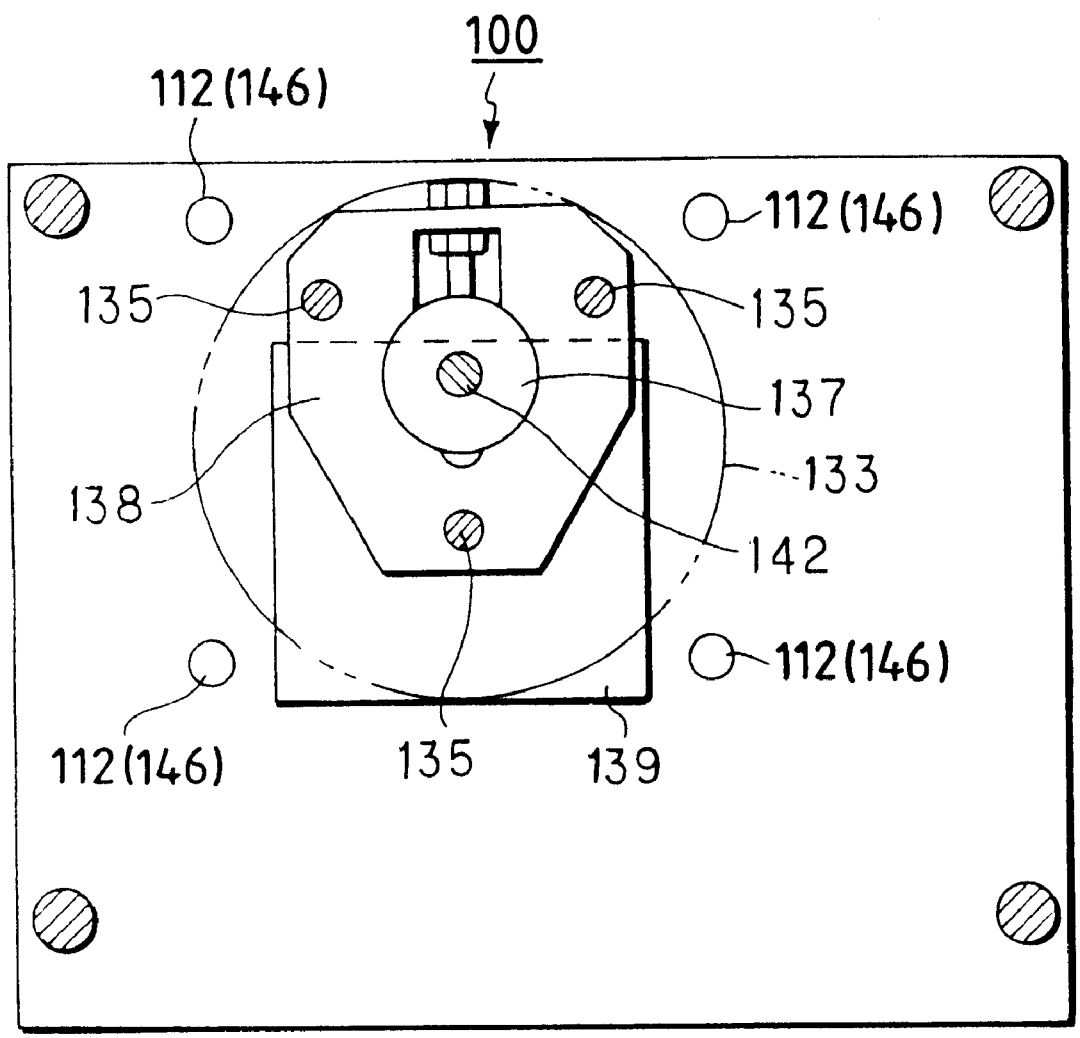
FIG. 12 is a section view taken along the line XII—XII of FIG. 11.

The plural support rods 135 stand from positions of the upper face of the eccentric rotating plate and separated by a predetermined distance from the rotation center (in the embodiment, three rods stand from positions corresponding to the vertices of a virtual triangle in FIG. 12). Each of the support rods 135 is configured so that the length to the tip end can be adjusted in a manual manner or another manner. In the embodiment, among the support rods 135, the one rod which is on the lower side in FIG. 12 is set to be longer than the other two rods by a given length. Alternatively, one rod may be set to be shorter than the other two rods by a given length.

Figure 14:
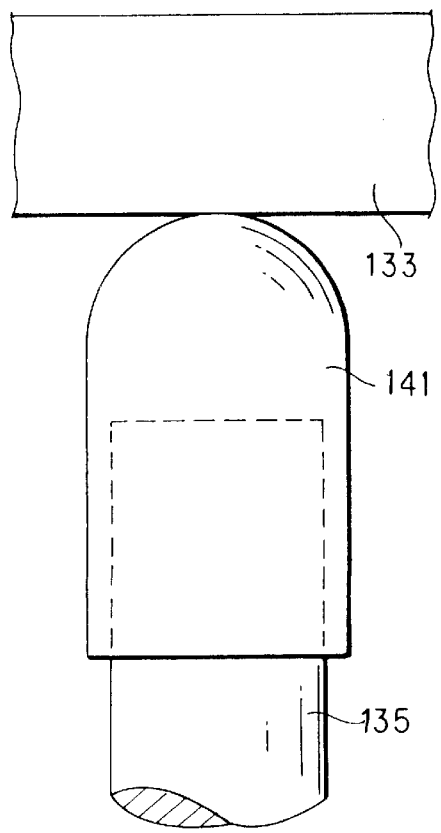
FIG. 14 is a schematic view showing a portion where a tip end of a support rod abuts against the base plate shown in FIG. 9.

As shown in FIG. 14, a cap 141 made of a wear-resistant resin such as MC nylon is screwed in a replaceable manner to the tip end of each of the support rods 135. In place of the cap 141, a roller made of a wear-resistant resin or the like may be rotatably supported on the tip end of each of the support rods 135.

As shown in FIGS. 9 to 12, and 14, the base plate 133 is supported by the support rods 135 which abut against the lower face via the caps 141. The base plate 133 is coupled to the boss portion 137 of the eccentric rotating crank 134 via a shaft 142 which passes through a substantially center portion of the plate and is fixed thereto, so as to be relatively rotatable and inclinable in a predetermined angle range.

Figure 13:
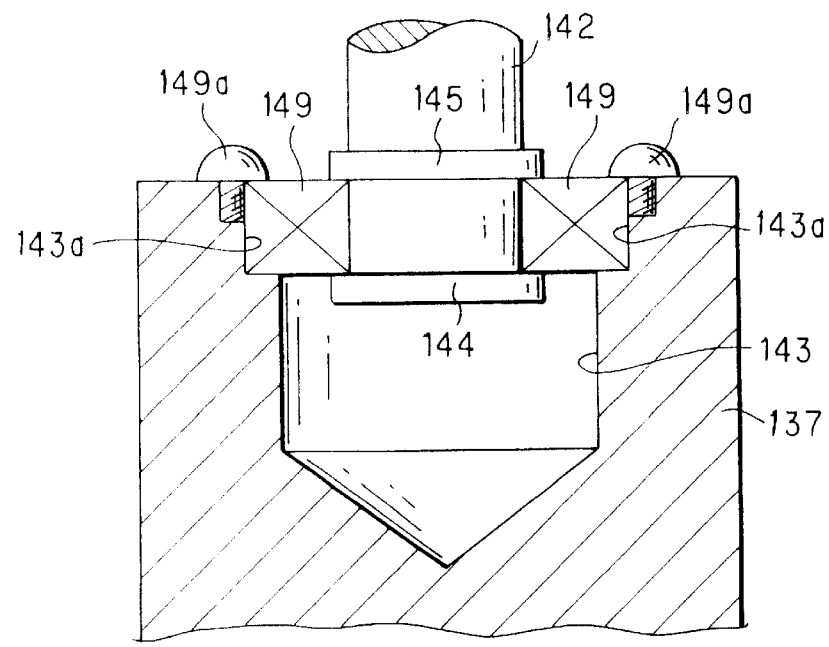
FIG. 13 is a schematic section view showing a portion where a shaft of a base plate shown in FIG. 9 is coupled to a boss portion of an eccentric rotating crank.

For example, as shown in FIG. 13, the shaft 142 of the base plate 133 is supported at the lower end portion by a self-aligning ball bearing 149 fixed to an opening edge 143a of a recess 143 which is formed in the boss portion 137 of the eccentric rotating crank 134. The lower end portion of the shaft 142 is positioned with respect to the inner race of the self-aligning ball bearing 149, by a lock ring 144 and a flange 145. The outer race of the self-aligning ball bearing 149 is fitted into the opening edge 143a and fixed thereto by locking screws 149a. Therefore, the shaft 142 is relatively rotatable and inclinable in the predetermined angle range with respect to the boss portion 137.

The inclination angle θ of the movable table 130 depends on the difference in length among the support rods 135, and can be suitably changed by adjusting the lengths of the support rods 135.

Plural (in the embodiment, four) spring members 146 are coupled at one end to positions of the lower face of the base plate 133 which are outer in a radial direction than the abutting positions of the support rods 135, respectively. The other ends of the spring members 146 are coupled to the upper end portions of fixing columns 112, respectively, so as to elastically restrict the horizontal movement of the base plate 133 within a predetermined range.

When the eccentric rotating crank 134 is eccentrically rotated in accordance with rotation of the motor 139, the eccentric rotating plate 138 moves in circular motion in a horizontal plane along predetermined forward and backward directions. At the same time, the support rods 135 and the boss portion 137 on the eccentric rotating plate 138 move together with the eccentric rotating plate 138 in circular motion in a horizontal plane along predetermined forward and backward directions.

In accordance with the circular motion of the eccentric rotating plate 138, therefore, the base plate 133 is moved in circular motion in a horizontal plane along predetermined forward and backward directions, in a state where the plate is inclined in a predetermined direction by the given angle θ from a horizontal plane by the difference in length among the support rods 135, and the inclination direction is changed along the peripheral direction of the circular motion in a horizontal plane in predetermined forward and backward directions. Therefore, the movable table 130 which is fixed to the base plate 133 via the columns 132 is caused to perform rocking motion in which the circular motion and the change of the inclination direction are combined with each other.

Figure 11:
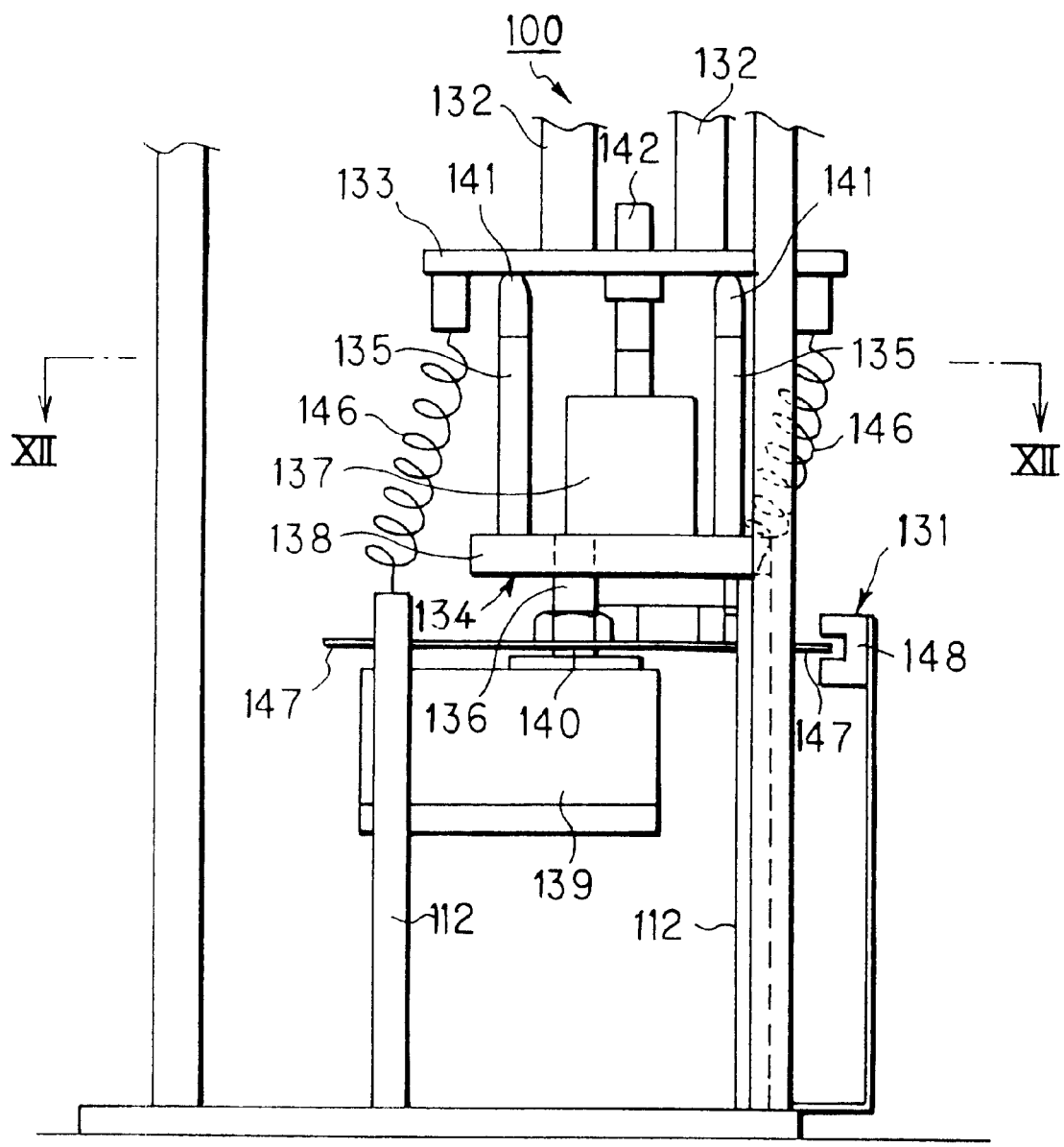
FIG. 11 is a schematic side view of the movable table shown in FIG. 9, looking in the direction of an arrow W.

As shown in FIG. 11, the constant-position detecting sensor 131 detects the position in the rotational direction of a constant-position detecting disk 147, by means of a sensor main unit 148, thereby detecting the reference position of the movable table 130.

The constant-position detecting disk 147 is fixed to a basal end portion of the shaft 136 of the eccentric rotating crank 134, in a substantially horizontal state. Consequently, the constant-position detecting disk 147 is rotated in accordance with rotation of the rotation shaft 140 of the motor 139, to be rotated in synchronization with the movable table 130. The position in the rotational direction of the constant-position detecting disk 147 is detected by detecting a notch (not shown) formed in a predetermined position of an outer edge portion, by means of the sensor main unit 148 of, for example, the optical type.

Figure 15:
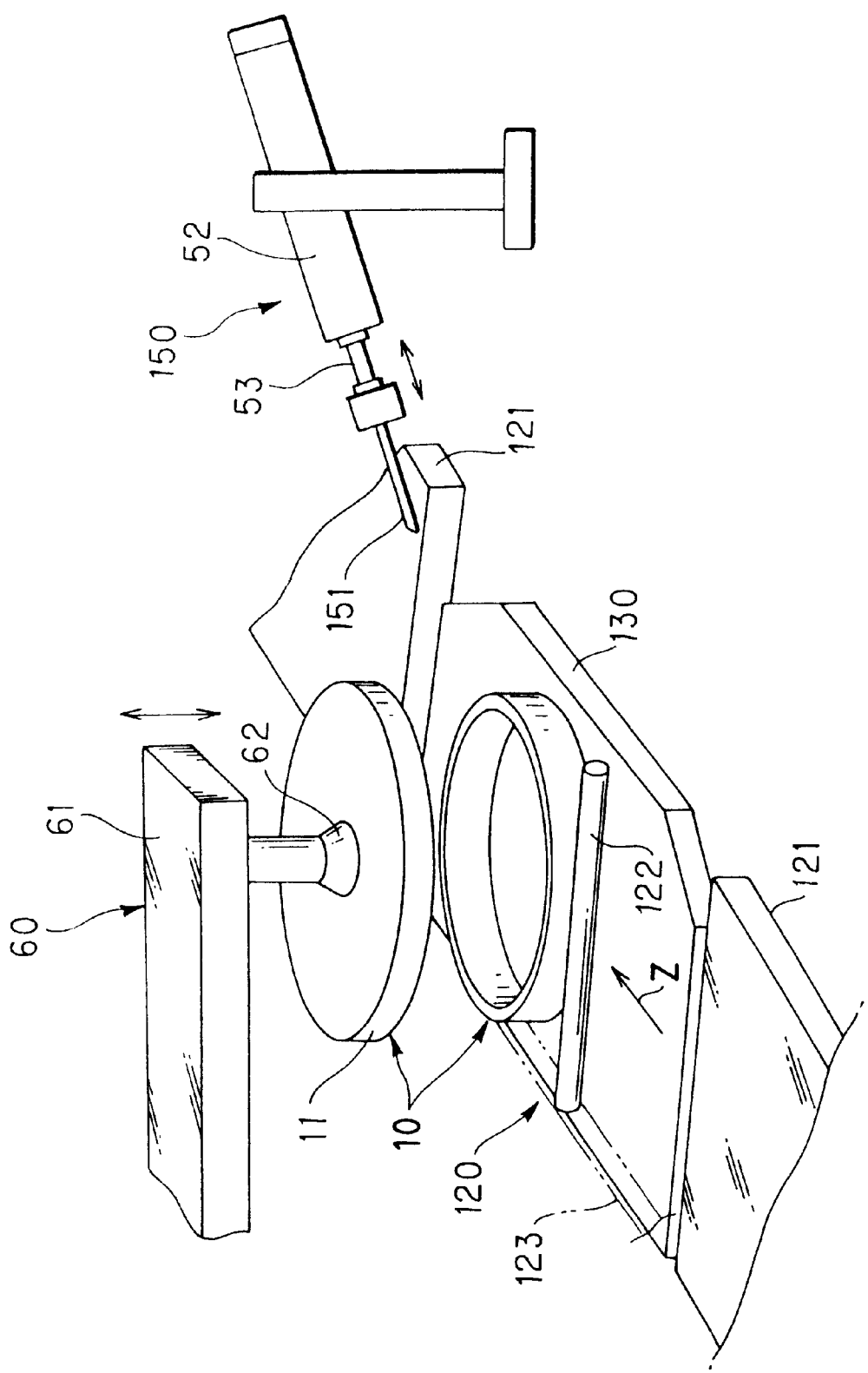
FIG. 15 is a schematic perspective view showing medium dispensing means and a lid holding mechanism of the medium dispensing apparatus shown in FIG. 9.

In the same manner as the medium dispensing means 50 of the first embodiment shown in FIG. 2, medium dispensing means 150 shown in FIG. 15 ejects a given amount of the medium from a medium dispensing nozzle 151 in a predetermined direction and at a given pressure. Specifically, the medium dispensing nozzle 151 is attached to a tip end of a cylinder rod 53 of an air cylinder 52. When the medium is to be dispensed, the nozzle is projected in a predetermined direction toward the laboratory dish 10 in accordance with the operation of the air cylinder 52, and a given amount of the medium is ejected by a predetermined ejection pressure due to a medium dispensing pump (not shown) of the roller type or the syringe type.

Figure 17A:
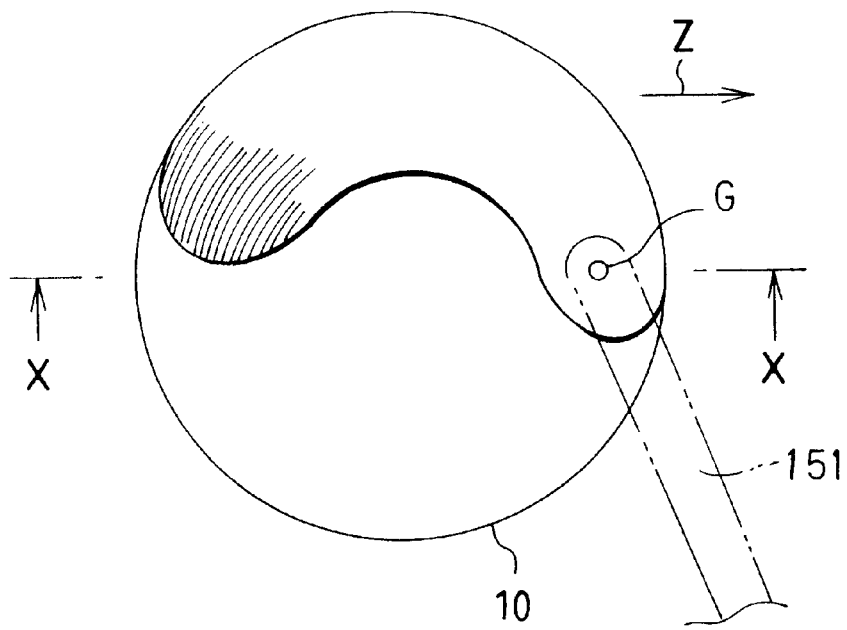
FIG. 17(a) to FIG. 17(b) are a plan view and a section view taken along the line X—X showing a laboratory dish to which a medium is dispensed by the medium dispensing means in production of a thin layer plate.
Figure 19A:
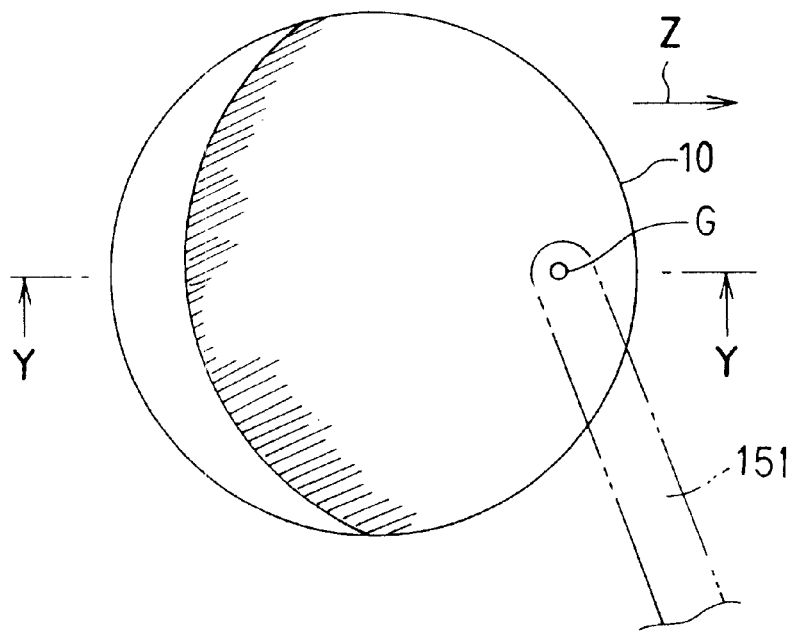
FIG. 19(a) to FIG. 19(b) are a plan view and a section view taken along the line Y—Y showing a laboratory dish to which a medium is dispensed by the medium dispensing means in production of a multilayer plate.

The medium dispensing means 150 dispenses the medium into the laboratory dish 10, toward a dispensation position G (see FIGS. 17(a) and 19(a)) which is higher in level than the center of the laboratory dish 10 on the movable table 130, so that at least part of a medium pool makes contact with the inner face of the side wall of the laboratory dish 10.

Figure 16A:
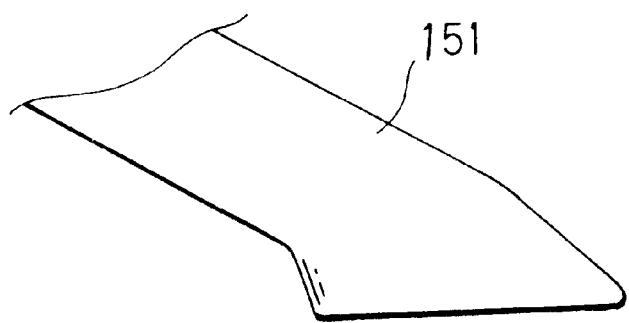
FIG. 16(a) to FIG. 16(b) are a side view and a bottom view showing the shape of a tip end of a medium dispensing nozzle of the medium dispensing means shown in FIG. 15.
Figure 16B:
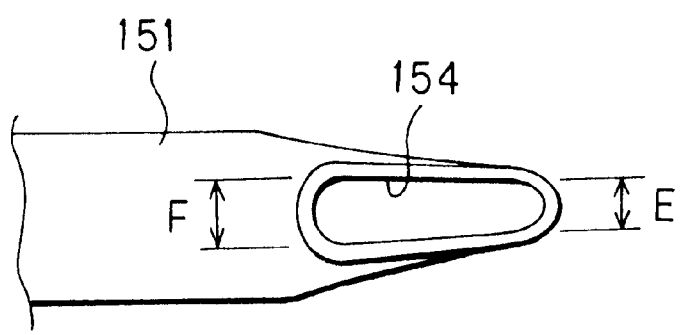

As shown in FIG. 16(a), the tip end of the medium dispensing nozzle 151 has a shape which is gradually widened in a side view as moving in the downward direction. As shown in FIG. 16(b), a passage opening 154 of the medium dispensing nozzle 151 is formed into an oval shape in which the longitudinal direction elongates along the flowing direction of the medium. For example, the dimension E is set to E=2 mm and the dimension F to F=2.5 mm.

As shown in FIG. 15, a lid holding mechanism 60 which is similar to the lid holding mechanism 60 of the first embodiment is disposed above the movable table 130.

Next, the function of the embodiment will be described with reference to FIGS. 17 and 18.

When dispensation of a thin layer plate is to be performed by the medium dispensing apparatus 100, for example, the laboratory dish 10 supplied from a laboratory dish supplying section (not shown) is transported to the movable table 130 by the laboratory dish transporting mechanism 120, and then placed on the movable table 130 (in the state shown in FIG. 2) which is in the reference position.

Figure 18A:
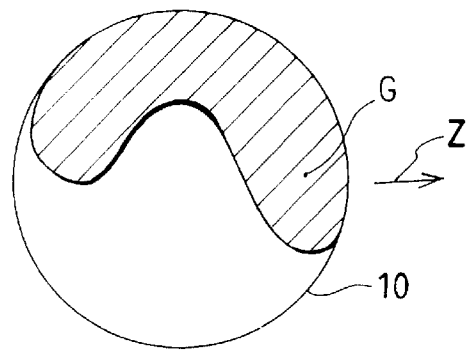
FIG. 18(a) to FIG. 18(d) are a plan view showing a state change of a medium which is dispensed into a laboratory dish shown in FIG. 17.
Figure 18B:
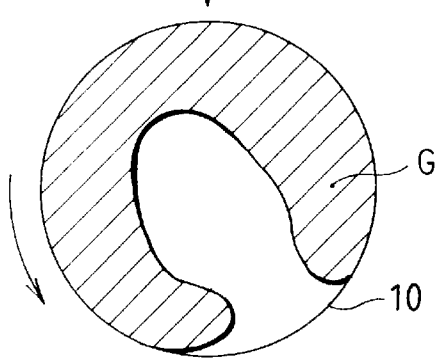

After the lid 11 is taken off by the lid holding mechanism 60, a given amount (about 5 cc) of the medium which previously contains viable cell is dispensed into the laboratory dish 10 on the movable table 130, from the medium dispensing nozzle 151 of the medium dispensing means 150. In this case, as shown in FIG. 17(a) and 18(a), the medium dispensing means 150 dispenses the medium into the laboratory dish 10, toward the dispensation position G which is higher in level than the center of the laboratory dish 10, so that at least part of the medium pool makes contact with the inner face of the side wall of the laboratory dish 10.

Figure 17B:
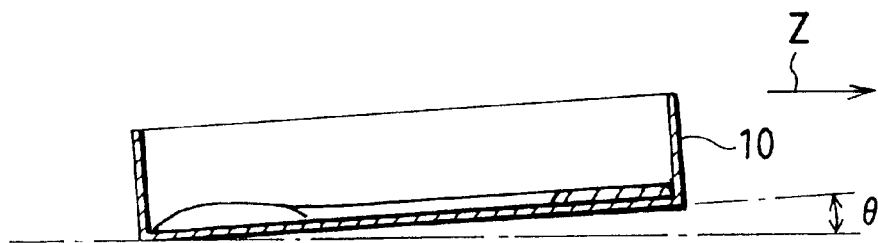

Since the movable table 130 is upward inclined by the given angle θ toward the downstream side in the transportation direction Z, the dispensed medium flows in the laboratory dish 10 toward the upstream side in the transportation direction Z as shown in FIG. 17.

The lid 11 is again put on the laboratory dish 10 to which the medium is dispensed, by the lid holding mechanism 60. Under this state, the movable table 130 is forward rotated for a predetermined time period (for example, 2.5 seconds), so that the laboratory dish 10 placed thereon is moved in circular motion in the forward direction (a counterclockwise direction in FIG. 18) along a horizontal direction, and is caused to change the inclination direction along the peripheral direction of the circular motion in a horizontal plane in the forward backward direction so as to perform rocking motion, while maintaining the inclination angle θ. As a result, as shown ill FIG. 18(b), the medium flows in a counterclockwise direction along the inner face of the side wall of the laboratory dish 10 so as to cover the downstream side in the transportation direction Z with respect to the center of the laboratory dish 10. In the movable table 130, the rotation in the flow direction in the case where the medium pool flows along the inner face of the side wall of the laboratory dish 10 as shown in FIG. 18(a) is set as the forward rotation.

Figure 18C:
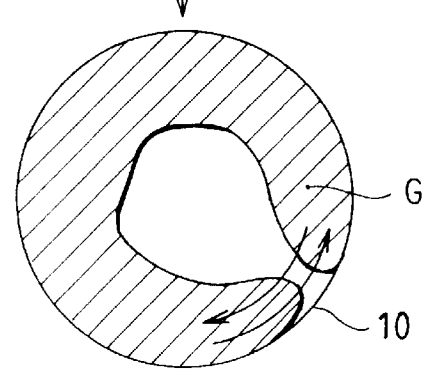
Figure 18D:
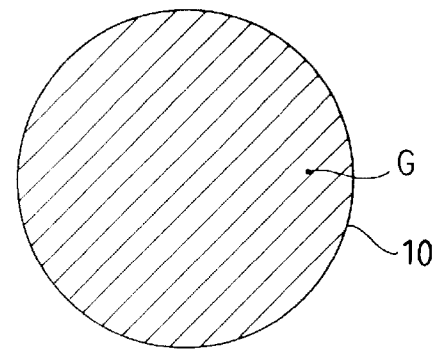

Next, the movable table 130 is stopped for a predetermined time period (for example, 0.5 seconds), and then backward rotated for a predetermined time period (for example, 2.5 seconds), so that the laboratory dish 10 is moved in circular motion in the backward direction (a clockwise direction in FIG. 18) along a horizontal direction, and is caused to change the inclination direction along the peripheral direction of the circular motion in a horizontal plane in the backward direction so as to perform rocking motion, while maintaining the inclination angle θ. As a result, as shown in FIGS. 18(c) and 18(d), the medium flows so as to cover also a center portion of the laboratory dish 11, and is hence uniformly spread.

After the medium in the laboratory dish 10 is uniformly spread by rocking motion of the movable table 130 in which the circular motion and the change of the inclination direction are combined with each other, the laboratory dish 10 is immediately transported to the next horizontal stage in which horizontality is ensured, and then allowed to stand still in a horizontal state for a predetermined time period (for example, 8 seconds). As a result, the medium in the laboratory dish 10 is uniformly solidified without causing an uneven thickness or the like.

Thereafter, the laboratory dish 10 is transported to a label attaching section (not shown). In the label attaching section, a label (not shown) bearing required information in the form of a bar code, such as the kind of the bacteria, the specimen number, and the date of dispensation is attached to the laboratory dish. The laboratory dish 10 to which the label is attached is transported to a laboratory dish stacking and accommodating section (not shown) to be accommodated therein.

Namely, according to the embodiment, the laboratory dish 10 which is placed on the movable table 130 and to which a given amount of the medium is dispensed by the medium dispensing means 150 is caused by the movable table 130 maintaining the inclination angle θ, to perform rocking motion in which the circular motion along a horizontal direction in the forward and backward directions, and a motion of changing the inclination direction along the peripheral direction of the circular motion in a horizontal plane in the forward and backward directions are combined with each other. As a result, flows of different directions are produced in the medium, and a flow of one direction collides with flows of other directions, so that the medium is uniformly dispensed.

Therefore, dispensation of the thin layer medium in which the medium hardly spreads because the dispensation amount of the medium is small (for example, about 5 cc) and the surface of the laboratory dish 10 has water repellency owing to a release agent which is used in molding of the plastic laboratory dish 10 can be satisfactorily performed.

In the third embodiment, the case of dispensation of a thin layer plate has been described. It is a matter of course that the embodiment may be used in preference also in dispensation of any of a plate medium, a poured culture plate, a multilayer medium, and a thin layer medium.

In the case of a multilayer medium, for example, the medium dispensing means 150 dispenses the medium into the laboratory dish 10, toward the dispensation position G which is higher in level than the center of the laboratory dish 10 as shown in FIG. 19(a), so that at least part of the medium pool makes contact with the inner face of the side wall of the laboratory dish 10.

Figure 19B:
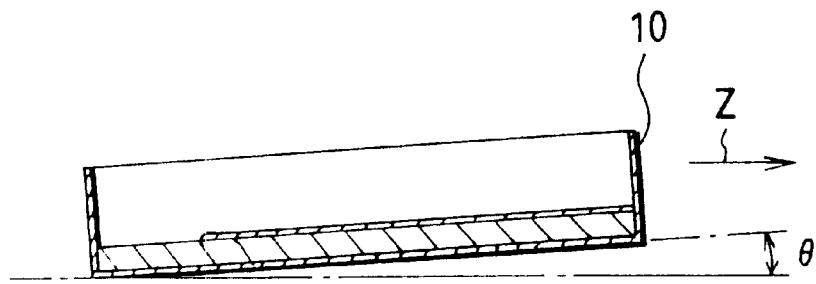
Figure 20:
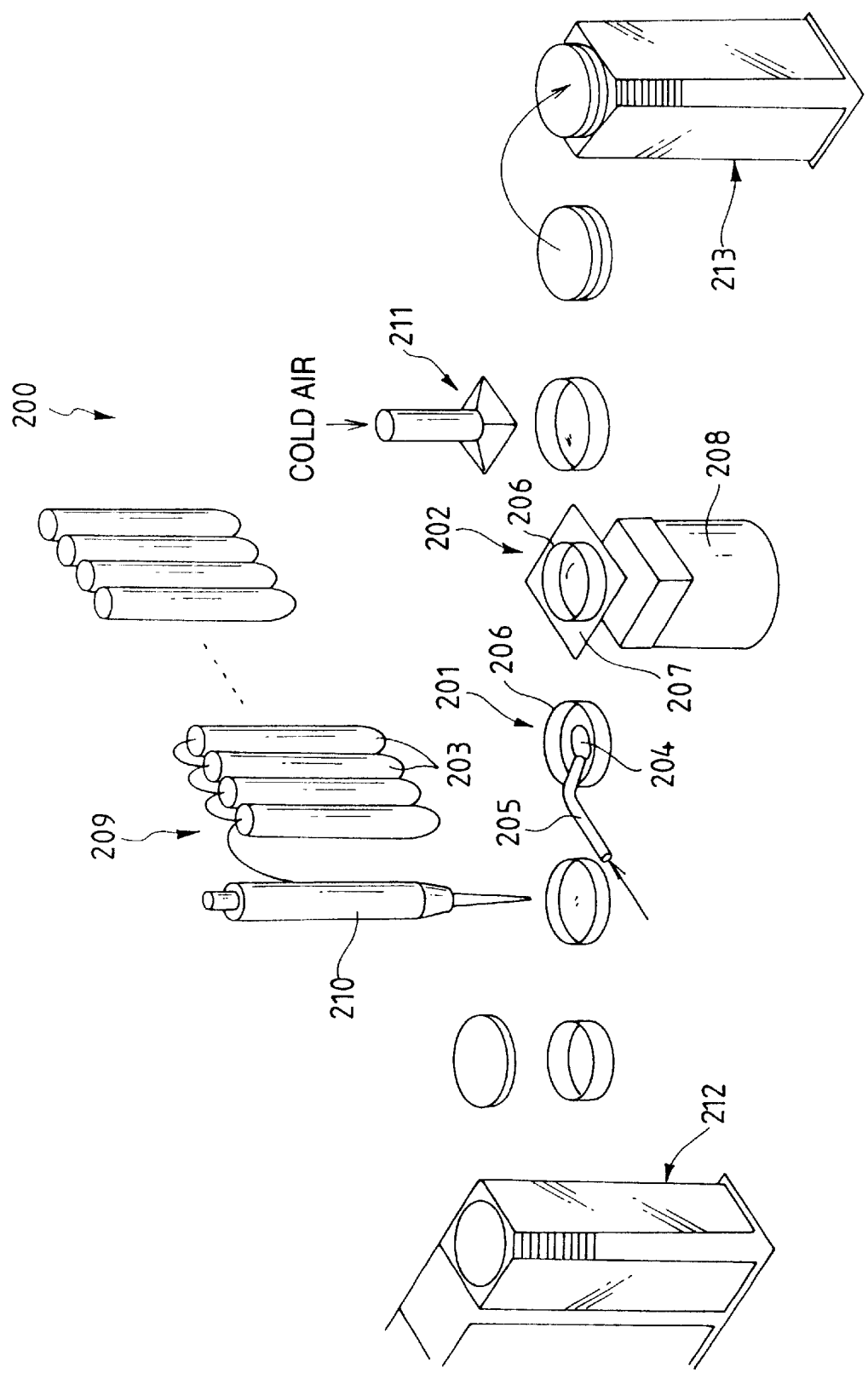
FIG. 20 is a view schematically showing the configuration of a conventional medium dispensing apparatus.

Since the movable table 130 is upward inclined by the given angle θ toward the downstream side in the transportation direction Z, the dispensed medium flows in the laboratory dish 10 toward the upstream side in the transportation direction Z as shown in FIG. 19(b).

In the same manner as the above-described case of a thin layer medium, the laboratory dish 10 to which the medium is dispensed is moved by the movable table 130 in circular motion in the forward and backward directions along a horizontal direction, and is caused to perform rocking motion with changing the inclination direction along the peripheral direction of the circular motion in a horizontal plane in the forward and backward directions, while maintaining the inclination angle θ. As a result, the medium flows so as to cover the whole interior of the laboratory dish 11, and is hence uniformly spread.

Therefore, it is possible to satisfactorily perform abovementioned dispensation of a multilayer medium in which the dispensation amount of the medium of the seed layer is small (for example, about 4 cc), the medium hardly spreads in a uniform manner during dispensation, and the temperature of the base layer that is previously solidified is lowered to the vicinity of room temperature (usually, 20 to 24° C.), and which is hence requested to be effectively processed for a short time period.

As described above, according to the third embodiment, by means of circular motion and a change of the inclination direction along the forward and backward directions of the base plate 133 due to rotation of the eccentric rotating crank 134 and the support rods 135, the movable table 130 causes the laboratory dish 10 placed thereon to perform rocking motion in which the circular motion and the change of the inclination direction are combined with each other.

Even when a small amount of the medium is used, therefore, an uneven thickness of the medium and the like can be surely prevented from occurring, and the embodiment can be satisfactorily used also in dispensation of any of a plate medium, a poured culture plate, a multilayer medium, and a thin layer medium. As a result, the work of dispensing any of a plate medium, a poured culture plate, a multilayer medium, and a thin layer medium can be automated, and the workability of such a dispensing work, the accuracy of a test, and the reliability can be improved.

The movable table 130 is controlled so as to stop always in the reference position, on the basis of the position detection signal from the constant-position detecting sensor 131. During dispensation of the medium by the medium dispensing means 150, therefore, the attitude of the laboratory dish 10 can be always kept constant. As a result, the shape of the medium immediately after dispensation into the laboratory dish 10 can be provided with constant reproducibility, and the medium can be spread more uniformly.

In the third embodiment, the movable table 130 is upward inclined by 4 degree toward the downstream side in the transportation direction Z. The present invention is not restricted to this. The inclination angle may be suitably selected in accordance with the kind of the agar medium, the dispensation amount, etc. The invention is not restricted to the configuration of the laboratory dish transporting mechanism 120, the movable table 130, and the medium dispensing means 150 of the embodiment, and may be variously configured.

Industrial Applicability

As described above, the medium dispensing apparatus and the method for the same of the invention are useful in the work of dispensing a medium in various kinds of tests such as microbial tests in, for example, the medicinal industry and relating to GMP validation, such as a axenic test; a bacteria limiting test; an environmental falling bacteria test; a measurement of the titer (efficacy) of an antibiotic; a body fluid concentration measurement; and a preservation effect test, microbial tests in, for example, the food industry, and relating to a countermeasure of preventing contamination due to noxious bacteria based on HACCP, such as a viable cell count test, and a fungus count test. Even when a small amount of a medium is to be dispensed, the medium can be satisfactorily dispensed, and an uneven thickness of the medium and the like can be surely prevented from occurring. The apparatus and the method are suitable for dispensation of any of a plate medium, a poured culture plate, a multilayer medium, and a thin layer medium.

What is claimed is:

1. A medium dispensing apparatus comprising:

a laboratory dish transporting mechanism which transports a laboratory dish along a predetermined path;

a movable table which is disposed in the laboratory dish transportation path by said transporting mechanism, which moves in circular motion in a horizontal plane along predetermined forward and backward directions, in a state where said table is inclined by a given angle with respect to a horizontal plane, and which changes an inclination direction along a peripheral direction of the circular motion in a horizontal plane in predetermined forward and backward directions, thereby causing said placed laboratory dish to perform rocking motion in which the circular motion and the change of the inclination direction are combined with each other; and a medium dispensing mechanism which dispenses a given amount of a medium into said laboratory dish placed on said movable table.

2. A medium dispensing apparatus according to claim 1, wherein said medium dispensing mechanism dispenses a given amount of the medium to a portion in said laboratory dish placed on said movable table, in a manner that at least part of the medium makes contact with an inner face of a side wall of said laboratory dish, the portion being higher in level than a center of said laboratory dish.

3. A medium dispensing apparatus according to claim 1 or 2, wherein said medium dispensing mechanism dispenses a given amount of the medium into said laboratory dish placed on said movable table in a reference position.

4. A method of dispensing a medium, comprising:

transporting a laboratory dish along a predetermined path by transporting mechanism, wherein said laboratory dish is placed on a movable table which is disposed in a laboratory dish transportation path by said transporting mechanism, dispensing a given amount of a medium by a medium dispensing mechanism into said laboratory dish placed on said movable table, and moving said movable table in circular motion in a horizontal plane along predetermined forward and backward directions, in a state where said moving table is inclined at a given angle with respect to a horizontal plane, wherein a direction of the inclination is changed along a peripheral direction of the circular motion in a horizontal plane in predetermined forward and backward directions, whereby said laboratory dish placed on said movable table is caused to perform rocking motion in which the circular motion and the change of the inclination direction are combined with each other.

5. A method of dispensing a medium according to claim 4, wherein said dispensing mechanism dispenses a given amount of the medium to a portion in said laboratory dish placed on said movable table, in a manner that at least part of the medium makes contact with an inner face of a side wall of said laboratory dish, the portion being higher in level than a center of said laboratory dish.

6. A method of dispensing a medium according to claim 4 or 5, wherein mechanism dispensing means dispenses a given amount of the medium into said laboratory dish placed on said movable table in a reference position.

* * * * *